United States Patent [19]

Howland

[11] Patent Number: 5,776,134

[45] Date of Patent: *Jul. 7, 1998

[54] LOW-PROFILE SPINAL FIXATION SYSTEM

[75] Inventor: Robert S. Howland, Seal Beach, Calif.

[73] Assignee: Advanced Spine Fixation Systems, Inc., Irvine, Calif.

[*] Notice: The term of this patent shall not extend beyond the expiration date of Pat. No. 5,520,687.

[21] Appl. No.: 471,637

[22] Filed: Jun. 6, 1995

Related U.S. Application Data

[62] Division of Ser. No. 219,748, Mar. 29, 1994, Pat. No. 5,520,687, which is a continuation of Ser. No. 938,868, Sep. 2, 1992, abandoned.

[51] Int. Cl.$^6$ .................... A61B 17/56; A61B 17/58; A61F 2/30
[52] U.S. Cl. .................... 606/61; 606/72; 606/73; 606/66
[58] Field of Search .................... 606/61, 60, 53, 606/57, 59, 64, 65, 69, 70, 72, 73, 66, 104; 623/13; 411/166, 169, 965, 968

[56] References Cited

U.S. PATENT DOCUMENTS

| 2,250,417 | 7/1941 | Ettinger | 606/59 |
|---|---|---|---|
| 2,742,938 | 4/1956 | Neuschotz | 411/270 |
| 3,130,765 | 4/1964 | Neuschotz | 411/108 |
| 4,483,334 | 11/1984 | Murray . | |
| 4,620,533 | 11/1986 | Mears | 606/54 |
| 4,653,481 | 3/1987 | Howland et al. | 17/56 |
| 4,719,905 | 1/1988 | Stepee | 606/61 |
| 4,772,448 | 9/1988 | Popalis | 376/463 |
| 5,000,165 | 3/1991 | Watanabe | 606/61 |
| 5,024,213 | 6/1991 | Asher | 606/61 |
| 5,030,220 | 7/1991 | Howland | 606/61 |
| 5,147,363 | 9/1992 | Harle | 606/72 |
| 5,217,497 | 6/1993 | Mehdian | 606/69 |
| 5,306,275 | 4/1994 | Bryan | 606/60 |
| 5,380,323 | 1/1995 | Howland | 606/61 |
| 5,429,639 | 7/1995 | Judet | 606/69 |
| 5,437,669 | 8/1995 | Yuan et al. | 606/61 |
| 5,486,174 | 1/1996 | Fournet-Fayard et al. | 606/73 |
| 5,520,678 | 5/1996 | Howland | 606/61 |

FOREIGN PATENT DOCUMENTS

| 111967 | 8/1991 | European Pat. Off. | 606/59 |
|---|---|---|---|
| 528706 | 2/1993 | European Pat. Off. | 606/61 |
| 2615095 | 3/1987 | France . | |
| 3032237 | 4/1982 | Germany . | |

OTHER PUBLICATIONS

William L. Carson, Ph.D., "Biomechanical Overview of the Isola Modular Spine Implant System. An Introduction", pp. 1–26. Sep. 16, 1989 Columbia, Missouri.
AcroMed Corporation, "Kaneda Anterior Spinal Instrumentation System Technique Manual", pp. 1–22.
DIMSO, "Spinal Fixation Diapason Device and Technique", pp. 1–5.
Sofamor Division Raquis, "Compact CD Lowback" Catalogo de los Productos, Brochure.

*Primary Examiner*—Robert A. Hafer
*Assistant Examiner*—Justine R. Yu
*Attorney, Agent, or Firm*—Christie, Parker & Hale, LLP

[57] ABSTRACT

The present invention relates to a low-profile screw-clamp assembly for use in spinal support fixation systems. The low-profile spinal fixation system comprises an anchor screw, a clamping assembly mounted on the anchor screw and a sleeve nut for attaching the clamping assembly to the anchor screw. The sleeve nut is substantially recessed into the clamping assembly, when the anchor screw and clamps are assembled. The present invention also relates to a locking mechanism, and method for making such a locking mechanism for locking the sleeve nut in place once assembled which comprises a crimp placed in a wall which forms the recess in the clamping assembly.

3 Claims, 7 Drawing Sheets

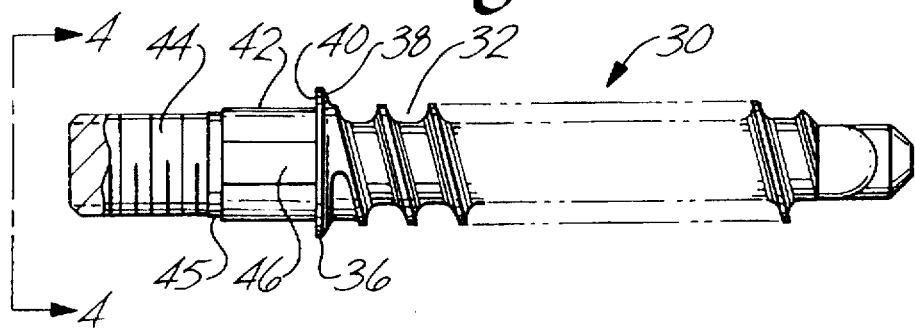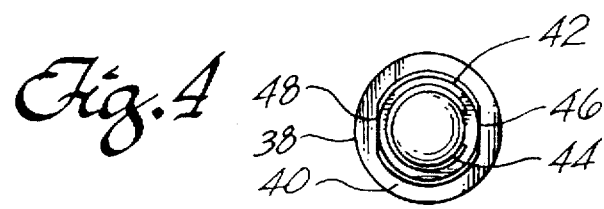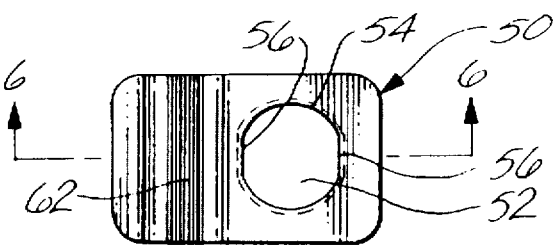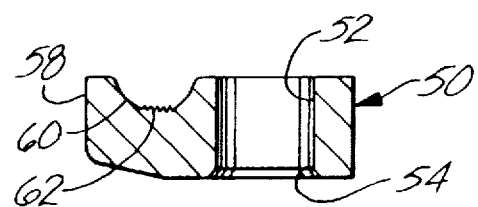

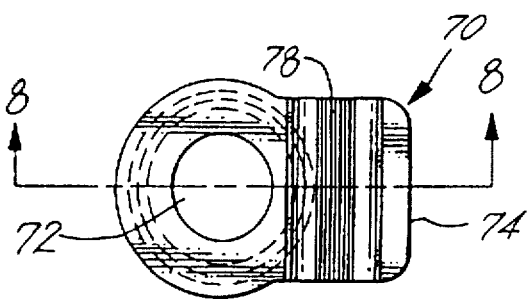
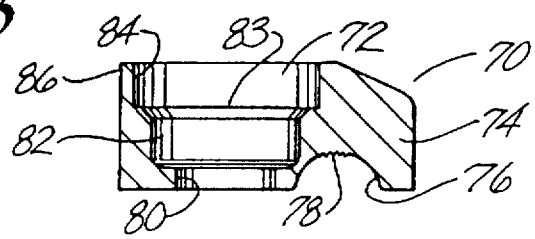
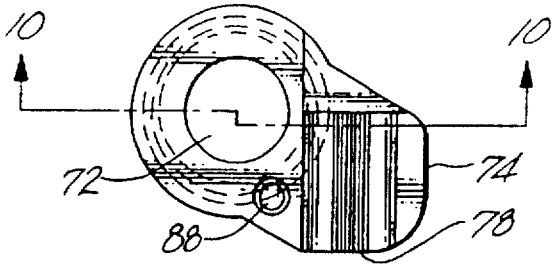
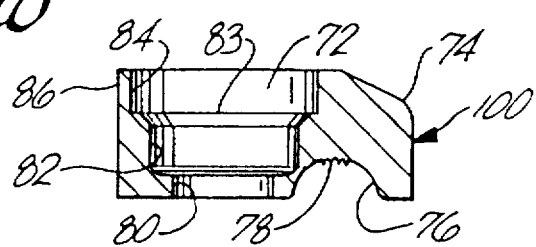

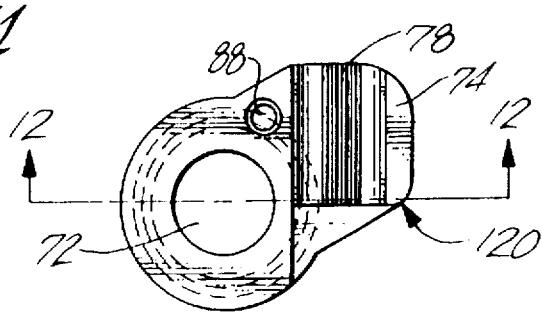
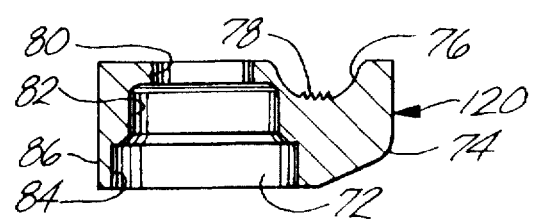
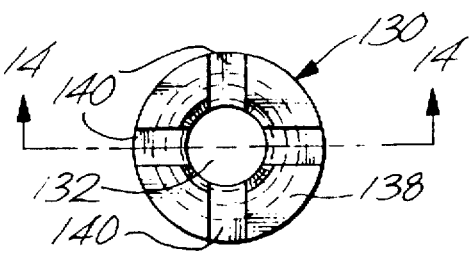
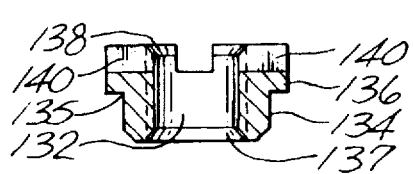

LOW-PROFILE SPINAL FIXATION SYSTEM

CROSS-REFERENCE TO RELATED APPLICATION

This is a division of application Ser. No. 08/219,748, filed Mar. 29, 1994, U.S. Pat. No. 5,520,687; which is a continuation of application Ser. No. 07/938,868, filed Sep. 2, 1992, now abandoned; and which are incorporated herein by reference.

FIELD OF THE INVENTION

This invention relates to an implantable, low-profile spinal fixation system for the surgical treatment of spinal disorders.

BACKGROUND OF THE INVENTION

Various types of spinal column disorders are known and include scoliosis (abnormal curvature of the spine), kyphosis (backward curvature of the spine), spondylolisthesis (forward displacement of a lumbar vertebra), and other disorders such as ruptured or slipped discs, broken or fractured vertebrae, and the like. Patients who suffer from such conditions usually experience extreme and debilitating pain. A technique known as spinal fixation, which results in the surgical/mechanical immobilization of areas of the spine and the eventual fusion of the treated vertebrae, has been used to treat such conditions and, in most cases, to bring to the patient a relief from pain. After the fusion of the vertebrae has occurred, the spinal fixation system is no longer required to immobilize the spinal region and could be removed if desired. However, it is preferable that the system is left in place, thus avoiding the necessity of subjecting the patient to a second surgery and to the possible complications associated with the surgery.

While it is preferable that the fixation system is left in place permanently, its presence can lead to the formation of a condition known as bursitis. Bursitis develops as the patient recovers from the surgical procedure of spinal fixation and resumes normal activities. The muscles of the back can rub over the nuts and clamps of the fixation system and become irritated. The muscles form a bursa or pad-like sac in response to the irritation, which may result in additional pain to the patient. To alleviate this pain, the patient is frequently subjected to additional surgery for the removal of the spinal fixation system.

It is desirable that a spinal fixation system is developed which, because it does not result in irritation of the back muscles, can be permanently left in place, thus avoiding the need to perform additional surgical procedures for the removal of the spinal fixation system. It is also desirable that the design of the system withstand lifelong implantation without requiring repairs or adjustments.

SUMMARY OF THE INVENTION

The present invention relates to a low-profile screw-clamp assembly for use in spinal support fixation systems. The low-profile spinal fixation system comprises an anchor screw, a clamping assembly mounted on the anchor screw and a sleeve nut for attaching the clamping assembly to the anchor screw. The sleeve nut is substantially recessed into the clamping assembly, when the anchor screw and clamps are assembled. This reduces protrusions above the clamp which may lead to irritation of the muscles which cover the clamping assembly when it is installed.

The present invention also relates to a locking mechanism, and method for making such a locking mechanism, which locks the sleeve nut in place once the clamping assembly has been attached to the anchor screw. The locking mechanism comprises a crimp, placed in a wall which forms the recess in the clamping assembly, to prevent rotation of the sleeve nut.

BRIEF DESCRIPTION OF THE DRAWINGS

Features, aspects and advantages of the invention will be more fully understood when considered with respect to the following detailed description, appended claims and accompanying drawings where:

FIG. 3 is a side view, partly in section and partly in elevation, of an anchor screw, in accordance with the present invention;

FIG. 4 is a top view, taken along the line 4—4 of FIG. 3;

FIG. 5 is a top view of the upper-side of a lower clamp assembly in accordance with the present invention;

FIG. 6 is a side view, partly in section and partly in elevation, taken along the line 6—6 of FIG. 5;

FIG. 7 is a bottom view of the underside of an upper clamp assembly in accordance with the present invention;

FIG. 8 is a side view, partly in section and partly in elevation, taken along line 8—8 of FIG. 7;

FIG. 9 is a bottom view of the underside of a right-handed offset upper clamp assembly in accordance with the present invention;

FIG. 10 is a side view, partly in section and partly in elevation, taken along line 10—10 of FIG. 9;

FIG. 11 is a bottom view of the underside of a left-handed offset upper clamp assembly in accordance with the present invention;

FIG. 12 is a side view, partly in section and partly in elevation, taken along the line 12—12 of FIG. 11;

FIG. 13 is a top view of the upperside of a sleeve nut in accordance with the present invention;

FIG. 14 is a side view, partly in section and partly in elevation, taken along the line 14—14 of FIG. 13;

DETAILED DESCRIPTION

The present invention relates to a "low-profile" spinal fixation system which reduces irritation to the back muscles which overlay the system once it has been installed. Previously-available spinal fixation systems, such as that described in U.S. Pat. No. 4,653,481, the disclosure of which patent is incorporated herein by reference, used two lock nuts which extended beyond the clamping assembly. This design required that the axial length of the top threaded end of the screw had to be of a dimension sufficient to accommodate the two nuts, thus increasing the axial length of the screw-clamp assembly. In some instances, the length of the screw-clamp assembly tended to cause muscle irritation after implantation. U.S. Pat. No. 5,030,220, the disclosure of which patent is incorporated herein by reference, described an improved spinal fixation system in which only a single nut, with a separate locking mechanism, was used. However, in this design the screw-clamp assembly still extended beyond the clamps and as a result still could result in muscle irritation. In the present invention, a sleeve nut fits into a recess on the upper surface of an upper half-clamp. The novel sleeve nut of the present invention greatly reduces the overall axial length of the screw-clamp assembly, resulting in a low profile and smooth upper surface of the fixation system which reduces the likelihood for the system's causing the formation of a painful bursa.

Figure 1:
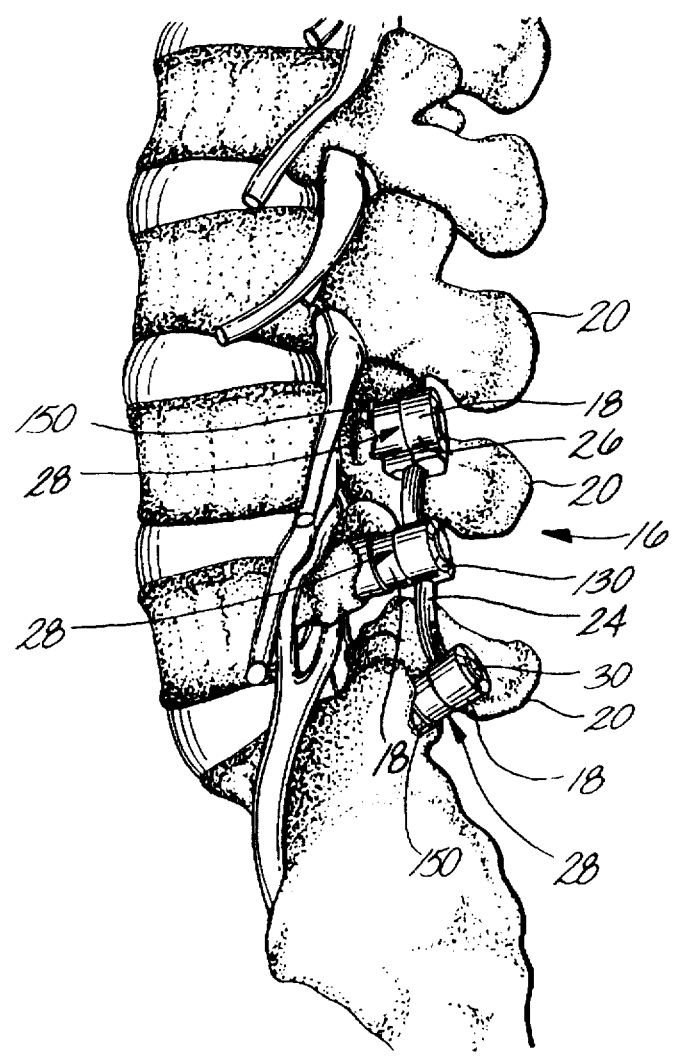
FIG. 1 is a diagrammatic lateral view of a spinal fixation system of the present invention, installed in a portion of the spinal column.
Figure 2:
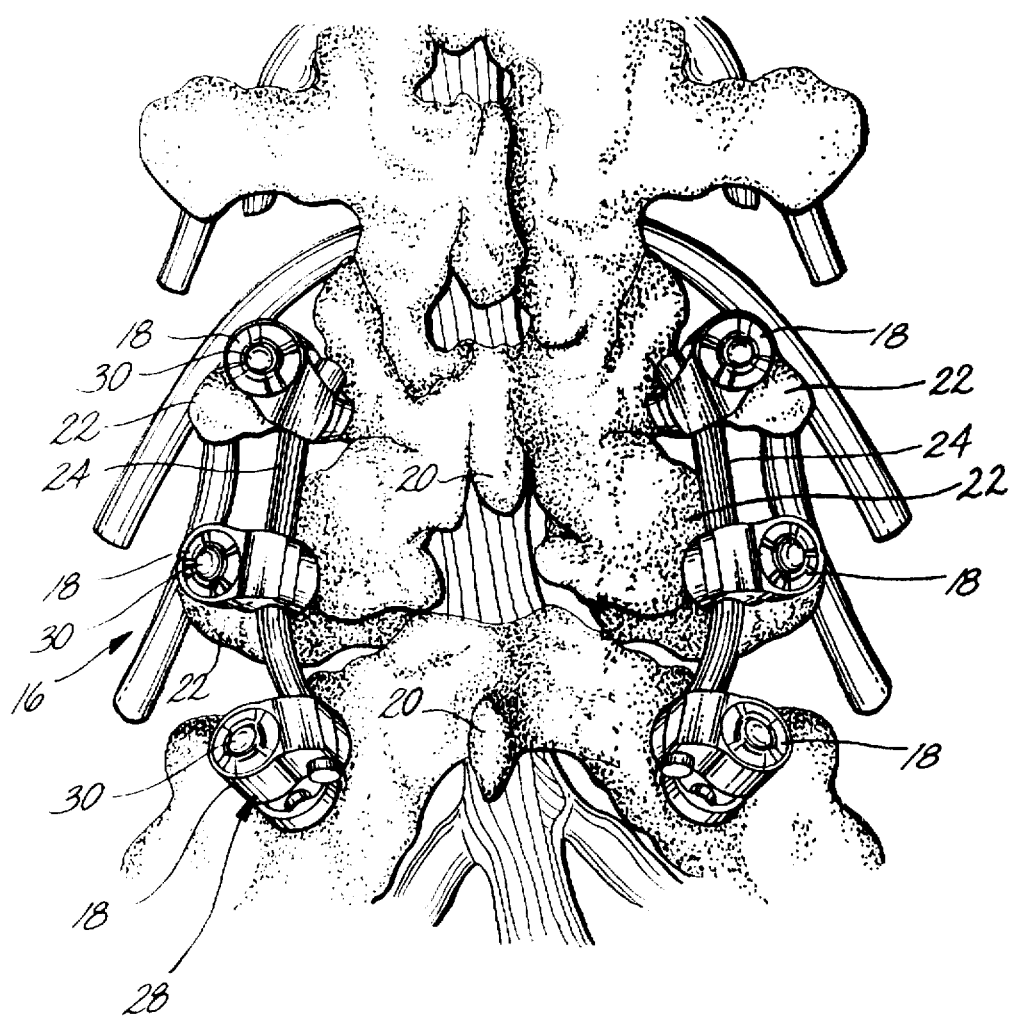
FIG. 2 is a diagrammatic posterior view of the spinal support fixation system illustrated in FIG. 1.

As illustrated in FIGS. 1 and 2, the spinal support system 16, is attached to S1, L5 and L4 vertebra to stabilize the spine in this region (although other attachment sites and corrections are also possible). The spine support system includes a plurality of screw-clamp assemblies 18, each of which is preferably located between the spinous process 20 and the associated transverse process 22 on each side of the spinous process and in the posterior portion of the spinal column. As shown, one screw-clamp assembly is placed in each side of each vertebra, and each of the screw-clamp assemblies supports and firmly holds a rod 24.

The screw-clamp assembly is attached to the pedicle by an anchor screw 30, which is shown in detail in FIGS. 3 and 4, to which is attached a clamp assembly 28. In accordance with a preferred embodiment of the invention, the clamp assembly is removable from the anchor screw and is preferably formed of a lower-half 50 and an upper-half 70, as shown in FIGS. 5-12. The upper- and lower-half clamps mate and firmly grip and purchase on the rod. The rod is serrated, as are the mating faces of the upper- and lower-half clamps. The upper- and lower-half clamps are attached to the anchor screw by a sleeve nut 130, which is shown in detail in FIGS. 13 and 14.

In FIGS. 1 and 2 the clamp assemblies are shown assembled medially, but can be reversed and assembled with the support rod laterally. The illustration also shows a spacer 150, alternate embodiments of which are shown in detail in FIGS. 15 and 16. The spacer allows for additional bone placement, raises the system to avoid impingement of inferior facets of the uninstrumented vertebrae, and creates a straighter support rod to simplify rod bending. The procedure for the mastering of the rod bending techniques are as described in an earlier patent, U.S. Pat. No. 4,653,481.

Referring now to FIGS. 3 and 4, the anchor screw 30 includes a lower-course threaded end 32 for placement and attachment of the screw-clamp assembly into the bony structure of the vertebrae of the spine. The preferred location is determined by the surgeon and is usually through the pedicle, although other regions, such as the sacral region, may be used. The screw-clamp assemblies may be inserted directly or they may be placed in predrilled openings, dimensioned to receive the threads of the anchor screw firmly in an appropriate support structure of the spine. The configuration of the anchor screw threads is well known in the art and is that which is normally used for screw members intended to be implanted in bone structures. The lower threaded end of the anchor screw terminates in a shoulder 36 which is tapered on a side 38 which abuts the lower threaded end of the anchor screw. The other side of the shoulder has a flat face 40. The provision of the shoulder permits the clamp assembly to be positioned close to the vertebra into which the anchor screw is positioned without the clamp assembly resting on the vertebra. The shoulder also inhibits anchor screw breakage and pullout of the anchor screw from the vertebra after installation, which could result from mechanical stresses placed on the anchor screw if the clamp assembly were resting on the vertebra.

Immediately adjacent the flat face of the shoulder is a generally-cylindrical clamp location section 42, whose diameter is less than that of the shoulder but greater than the major diameter of an adjacent upper threaded end 44. A fillet radius 45 is located at the junction of the clamp location section and the upper threaded end. The generally-cylindrical clamp location section includes two flat sections 46 and 48, located 180 degrees from each other, which operate as locators for the lower-half clamp to prevent rotation of the lower-half clamp relative to the anchor screw when the anchor screw and clamp are assembled.

The anchor screw, as well as the other components, is preferably made of 316 LVM stainless steel, which is electro-polished and passivated to resist corrosion by body fluids. The anchor screws come in various lengths and diameters to accommodate the need of the surgeon in attaching the spinal fixation system.

FIGS. 5 and 6 illustrate the structure of the lower-half clamp 50 of the clamp assembly. The lower-half clamp is provided with an aperture 52 for receipt on the clamp location section 42 of the anchor screw 30. A chamfer line 54 is located on the lower surface of the lower-half clamp. The lower-half clamp is assembled such that its bottom surface is seated on the shoulder 36. The aperture is provided with opposing flat surfaces 56, which mate with flat surfaces 46 and 48 on the clamp location section of the anchor screw. The axial length of the lower half-clamp is approximately that of the axial length of the clamp location section. The lower-half clamp also includes an arm 58 which forms a rod-receiving half-aperture 60, laterally of the aperture 52. The rod-receiving half-aperture is serrated along its length, as indicated at 62, for mating with and gripping the serrated rod.

FIGS. 7 and 8 illustrate an upper-half clamp 70, which is provided with an aperture 72 for receipt on the upper threaded end 44 of the anchor screw 30. The axial length of the upper-half clamp is greater than that of the upper threaded end 44 of the anchor screw so that, when assembled, none of the threaded portion extends beyond the upper-half clamp 70.

The internal diameter of the upper-half clamp is stepped. A lower section 80 has a diameter such that, when placed on the anchor screw, the upper-half clamp will fit securely against the threaded section 44 of the anchor screw. An intermediate section 82, which abuts the lower section, has an intermediate diameter which is greater than the diameter of the lower section. Adjacent the intermediate section is an upper section 84, which has a diameter larger than that of the intermediate section. The intermediate and upper sections are separated by a chamfer line 83. When assembled, the intermediate and upper sections accommodate a sleeve nut 130, which is described in detail below.

The upper-half clamp also includes an arm 74 which forms a rod-receiving half-aperture 76, laterally of the aperture 72. The rod-receiving half-aperture is serrated along its length, as indicated at 78, for mating and gripping the serrated rod. When assembled, the serrated surfaces of the upper- and lower-half clamps are in facing relation to each other and mate with and firmly grip the serrated rod.

FIGS. 9–12 illustrate alternative embodiments for the clamp assemblies of the present invention. Illustrated are upper-half clamps 100 and 120, respectively, for a right-hand offset and a left-hand offset, respectively. Not illustrated are matching right- and left-handed offset lower-half clamps, although it will be understood by one skilled in the art that such lower-half clamps would be structured to mate with the respective upper-half clamps described. Since these upper-half clamps have parts that are essentially the same as parts of those previously described, the same reference numerals are used for the same parts. The positioning of a right-hand offset clamp is shown in FIG. 2, attached to the L4 vertebra. These offset half-clamps are convenient for avoiding contact with facets of the vertebrae, where the straight half-clamps would interfere with the surrounding bone of the facets. In one embodiment of the present invention the right-and left-hand offset upper-half clamps include a pin-clearance hole which mates with a pin located on the lower-half clamp, not shown. The pin and clearance-hole prevent rotation of the upper- and lower-half clamps, relative to each other when they are assembled. When assembled, the lower- and upper-half clamps are placed on the anchor screw, as described above. A sleeve nut is used to hold the lower- and upper-half clamps in place on the anchor screw face 40 and to ensure a firm grip on the rod. The sleeve nut is illustrated in FIGS. 13 and 14. The sleeve nut 130 has an aperture 132, which is threaded so that it mates with the threaded portion 44 of the anchor screw.

The exterior of the sleeve nut is of different diameters. At the lower end of the sleeve nut, the diameter of the sleeve nut 134 is at its smallest and is sized such that the sleeve nut will fit into the stepped region 82 of the upper-half clamp. At the upper end of the sleeve nut, and adjacent the small-diameter portion 134, is a large-diameter portion of the sleeve nut 136. A fillet radius 135 is located at the juncture of the small- and large-diameter portion of the sleeve nut. The large-diameter portion is sized so that it will fit into the stepped region 84 of the upper-half clamp, thus holding the upper-half clamp and the lower-half clamp securely in place when the sleeve nut is screwed onto the anchor screw. The stepped interior of the upper-half clamp allow a distribution of the force conferred by the sleeve nut on the upper-half clamp over a larger area. A chamfer line 137 is locate at the bottom of the sleeve nut. When the sleeve nut is tightened onto the anchor screw the chamfer line 137 will not engage the fillet radius 45 of the anchor screw.

Figure 17:
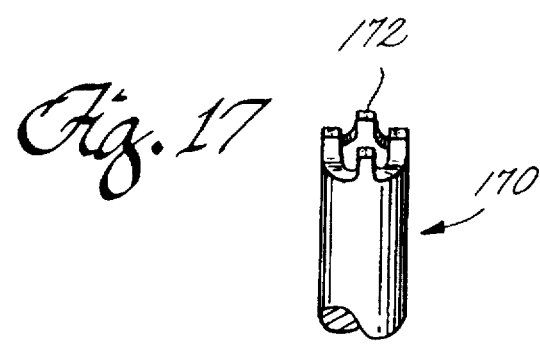
FIG. 17 is a perspective view of a driver in accordance with the present invention.

The top face 138 of the sleeve nut includes four radial notches 140, placed at equal distances from each other. The notches align with prongs 172 of a driver 170, such as that illustrated in FIG. 17. In one embodiment of the present invention the driver is attached to a torque wrench for tightening the sleeve nut into the upper-half clamp to ensure that the correct pressure is applied. Preferably the sleeve nut is tightened to about 100 in. lb of torque. In a preferred embodiment the driver comprises a mechanism for holding the sleeve nut so that the surgeon can more easily attach the sleeve nut to the anchor screw.

In use, the lower-half clamp is assembled over an anchor screw, and then, after the rod is in position, the upper half-clamp is installed. The sleeve nut is then threaded on the upper threaded-end portion of the anchor screw and tightened down, using driver 170. The prongs of the driver are mated with the notches of the sleeve nut and the driver is then used to tighten the sleeve nut into the upper-half clamp. The sleeve nut, when tightened down, is completely contained within the aperture 72, leaving exposed a small portion of the upper edge of the wall 86 of the upper-half clamp.

Figure 18:
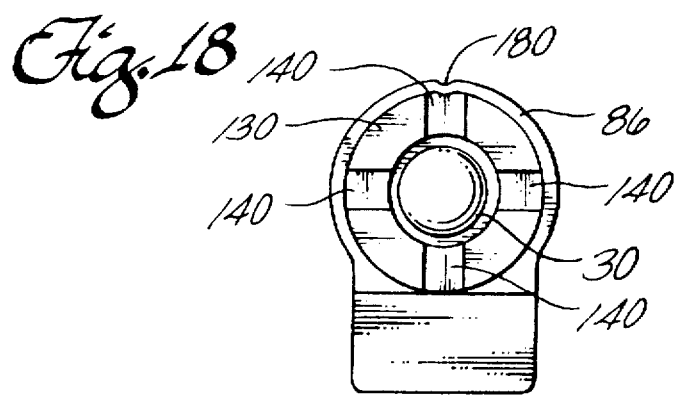
FIG. 18 is a top view, partly in section and partly in elevation, of a clamp assembly in accordance with the present invention.
Figure 19:
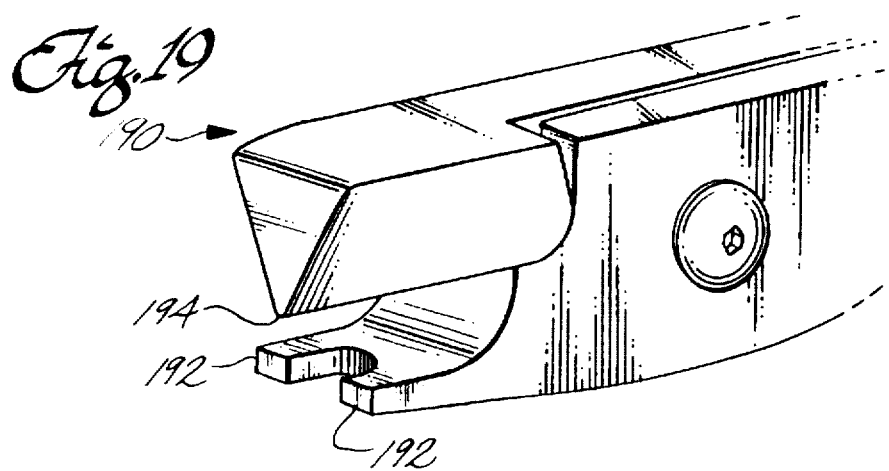
FIG. 19 is a perspective view of the jaws of a crimping pliers in accordance with the present invention.

After the sleeve nut is in place, the exposed portion of the wall 86 is crimped at one point along its periphery corresponding to one of the radial notches as illustrated in FIG. 18. The crimp 180 ensures that the sleeve nut is firmly locked in place and that undesired rotation of the sleeve nut is inhibited. The crimp can conveniently be made using a tool such as that illustrated in FIG. 19. The tool 190 is a pliers type tool with one of the jaws comprising two prongs 192 and the other jaw comprising a projection 194. The prongs are placed in two radial notches, across the diameter of the sleeve nut. The pliers are then closed to bring the projection of the second jaw in contact with the outside edge of the upper-half clamp, thus forming a crimp.

In the event that some adjustment, and hence removal of the sleeve nut is necessary, the crimp is easily overcome by using the driver to remove the sleeve nut, and the sleeve nut is unscrewed to release the upper- and lower-half clamps. After any required adjustment has been made, the screw-and-clamp assembly is secured in place, as described above.

Figure 15:
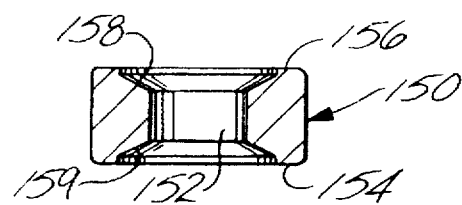
FIG. 15 is a side view, partly in section and partly in elevation of a spacer in accordance with the present invention.

Occasionally, it is desired to raise the clamp assembly to a given plane, in order to have the various clamping surfaces in planar alignment, or to have one or more clamping surface(s) elevated with respect to the remainder. FIG. 15 illustrates a spacer 150, which is received between the bottom face 38 of shoulder 36 on anchor screw 30 and the bone or sacrum (see FIG. 1, for example). The spacer is provided with an aperture 152 for passage of the threaded portion 32 of the anchor screw, but the latter is not screwed into the spacer. Since anchor screws of various lengths and diameters may be used, the aperture of the spacer may vary with the particular anchor screw. Further, since various heights may be needed, the axial length of the spacer may vary. While the spacers increase the profile of the clamping assembly they are often desirable so that the system as a whole remains in a single plane and so that the rod does not have to be bent excessively.

The principal function of the spacer, in addition to providing added height to the clamp assembly, is to provide support for the anchor screw, since not all of the threaded portion of the anchor screw may be inserted into the bone. In use, the spacer is placed over the threaded portion 32 of the anchor screw. The anchor screw is then placed into the bone until the bottom face 154 of the spacer contacts the bone. As illustrated, each of the faces 154 and 156 is provided with a chamfer line 158 to mate with the tapered side 38 of the shoulder of the anchor screw, thus maintaining the two in alignment. It is apparent that either face 154 or 156 may be the bottom or upper face of the spacer.

Figure 16:
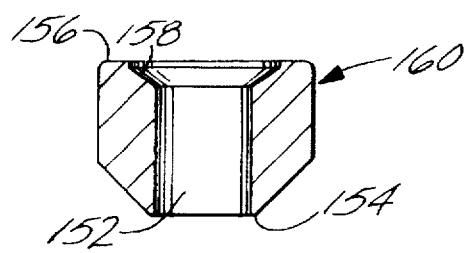
FIG. 16 is a side view, partly in section and partly in elevation, of a tapered spacer in accordance with the present invention.

On other occasions, it is desirable to not only raise the clamp assembly, but also to reduce the amount of metal in contact with the bone. Such may be the case where the clamp assembly is placed on the pedicles of the lumber vertebrae. In such cases, the use of a tapered spacer is desirable to minimize the need to modify the pedicles to seat the spacer on the vertebrae. FIG. 16 illustrates a tapered spacer 160. Since the tapered spacer has parts that are essentially the same as parts of the spacer previously described, the same reference numerals are used for the same parts. The tapered spacer differs from the previously-described spacer in that the lower face 154 is not interchangeable with the upper face 156.

Figure 20:
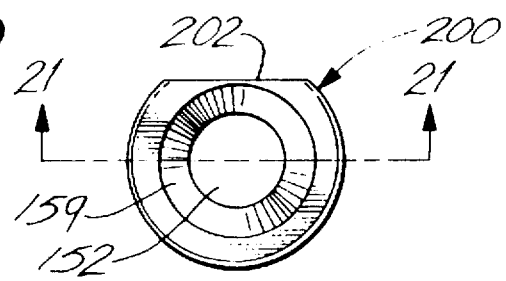
FIG. 20 is a top view, partly in section and partly in elevation of a "D"-spacer in accordance with the present invention.
Figure 21:
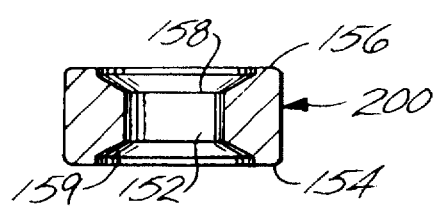
FIG. 21 is a side view, partly in section and partly in elevation, of a "D"-spacer taken along the line 21—21 of FIG. 20.

In another embodiment of the present invention a "D"-spacer 200 is used, as illustrated in FIGS. 20 and 21. Since the "D"-spacer has parts that are essentially the same as parts of the spacer previously described, the same reference numerals are used for the same parts. The flat face 202 of the "D"-spacer allows the spacer to be placed close to the lateral side of the superior facets of the vertebrae.

The advantage of the spinal fixation system of the present invention is, that the axial length (height) of the screw-clamp assembly is greatly reduced, when compared to the height of previously-available screw-clamp assemblies, since the axial length of previous screws had to be of a dimension sufficient to accommodate at least one nut and locking washer above the clamp. The height of the screw-clamp assembly as installed increased the probability of muscle irritation by the clamp assembly. Also, the installed fixation system has a top surface which is in a single plane which reduces muscle irritation. In the present invention, the sleeve nut fits into a recess on the upper surface of the upper-half clamp, greatly reducing the overall axial height of the anchor screw above the upper-half clamp. This low profile of the fixation system reduces the likelihood of the system's causing the formation of a painful bursa.

The present invention is not limited to the specific designs shown. Therefore, the present invention is not intended to be limited to the working embodiments described above. The scope of the invention is defined in the following claims.

What is claimed is:

1. A low-profile screw-clamp assembly for use in spinal support fixation systems comprising:

an anchor screw having a lower threaded end portion for attaching the screw-clamp assembly to a vertebra, an upper threaded end, and a substantially cylindrical shoulder disposed between the upper and lower threaded ends;

a clamping assembly mounted on the substantially-cylindrical shoulder of the anchor screw comprising an upper-half clamp having an enclosed recessed upper surface and a lower-half clamp which mates with the upper-half clamp to form a rod-receiving aperture; and a sleeve nut for attaching the clamping assembly to the upper threaded end of the anchor screw, wherein the sleeve nut fits into the enclosed recess on the upper surface of the upper-half clamp to provide a substantially smooth outer surface so as to reduce irritation to the muscles of the back when a system is implanted.

2. A low-profile screw-clamp assembly as recited in claim 1 wherein the enclosed recess on the upper surface of the upper-half clamp is defined by a wall and the sleeve nut is locked into the clamping assembly by a crimp placed in the wall of the upper-half clamp.

3. A low-profile clamp assembly for use in the fixation of a patient's spine comprising:

a spine rod;

an anchor member for anchoring the assembly to the patient's spine, the anchor member including an upper threaded end portion;

a clamp having first and second clamping portions for pressing toward one another to clamp the rod, the first clamping portion including a thin plastically deformable wall around its perimeter defining a recessed upper surface; and a sleeve nut including at least one radial notch and an inner threaded surface for mating with the upper threaded end portion of the anchor member to press the first and second clamping portions toward one another to clamp the rod, wherein the sleeve nut fits into the recessed upper surface of the first clamping portion to provide a substantially smooth outer surface to the first clamping portion and the plastically deformable wall can be crimped to protrude into the at least one radial notch of the sleeve nut to prevent rotation of the sleeve nut within the first clamping portion.

\* \* \* \* \*